US00PP35237P2

(12) United States Plant Patent
Moucheboeuf

(10) Patent No.: US PP35,237 P2
(45) Date of Patent: Jun. 27, 2023

(54) DIANTHUS PLANT NAMED 'WP22 PIE68'

(50) Latin Name: ***Dianthus allwoodii* hort.**
Varietal Denomination: WP22 PIE68

(71) Applicant: Plant Genetics International, Ltd., Exeter (GB)

(72) Inventor: Laetitia Moucheboeuf, Devon (GB)

(73) Assignee: Plant Genetics international, Ltd, Exeter (GB)

( * ) Notice: Subject to any disclaimer, the term of this patent is extended or adjusted under 35 U.S.C. 154(b) by 0 days.

(21) Appl. No.: 18/053,969

(22) Filed: Nov. 9, 2022

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./272, 273, 277
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Dianthus* plant named 'WP22 PIE68' that is characterized by a compact mounding habit, large single vibrant magenta flowers, blooming from May through October, with a medium, clove like fragrance, glaucous blue green foliage, suitable for use as a flowering plant in pots and containers as well as for use as a cut flower and in bouquets, is disclosed.

2 Drawing Sheets

Genus and species: *Dianthus allwoodii* hort.
Variety denomination: 'WP22 PIE68'.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus allwoodii* hort. and will be referred to hereinafter by the cultivar name 'WP22 PIE68'.

'WP22 PIE68' is a complex hybrid plant that is the product of a long-term breeding program conducted in a cultivated area of Ashcombe Road, Dawlish, Devon, United Kingdom. 'WP22 PIE68' was selected in 2016 for its large single vibrant magenta flowers, medium clove like fragrance and glaucous blue-green foliage.

'WP22 PIE68' arose and was selected as a seedling which resulted from the controlled pollination of two prior selections of *Dianthus*. The male parent is *Dianthus* code name 'GI539' (unpatented and unreleased) and the female parent is *Dianthus* code name 'GI416' (unpatented and unreleased). The male parent and female parent had both grown within the inventor's stock of breeding lines.

Asexual reproduction of 'WP22 PIE68' was first accomplished in 2016 in a cultivated area of Ashcombe, United Kingdom using the propagation method of shoot cuttings. 'WP22 PIE68' has been determined to be stable and reproduces true to type in successive generations of asexual propagation.

SUMMARY

The following traits have been repeatedly observed and represent the characteristics of the new *Dianthus* cultivar 'WP22 PIE68'. 'WP22 PIE68' has not been tested under all possible conditions and phenotypic differences may be observed with variations in environmental, climatic and cultural conditions, however, without any variance in genotype.

1. 'WP22 PIE68' exhibits a compact mounding habit.
2. 'WP22 PIE68' bears large single vibrant magenta flowers.
3. The petals of 'WP22 PIE68' are wavy.
4. 'WP22 PIE68' blooms from May through October.
5. The flowers of 'WP22 PIE68' exhibit a medium, clove like fragrance.
6. 'WP22 PIE68' exhibits glaucous blue green foliage.
7. At maturity, the height of the foliage mound of 'WP22 PIE68' is 40 cm, and the width is 30 cm.
8. 'WP22 PIE68' is perennial and is hardy at least to minus 15° Centigrade.
9. 'WP22 PIE68' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP22 PIE68' showing colors as true as it is reasonably possible to obtain in colored reproductions of this type. Colors in the photographs may differ from the color values cited in the detailed botanical description, which accurately describe the actual colors of the new variety 'WP22 PIE68'.

Figure 1:
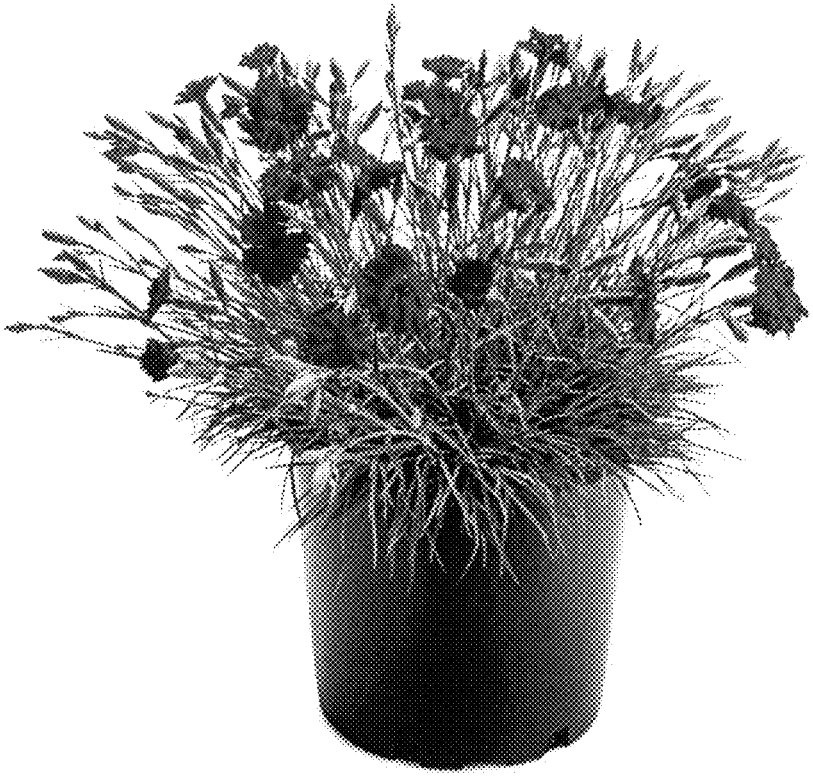
FIG. 1 depicts an entire flowering plant of 'WP22 PIE68'.
Figure 2:
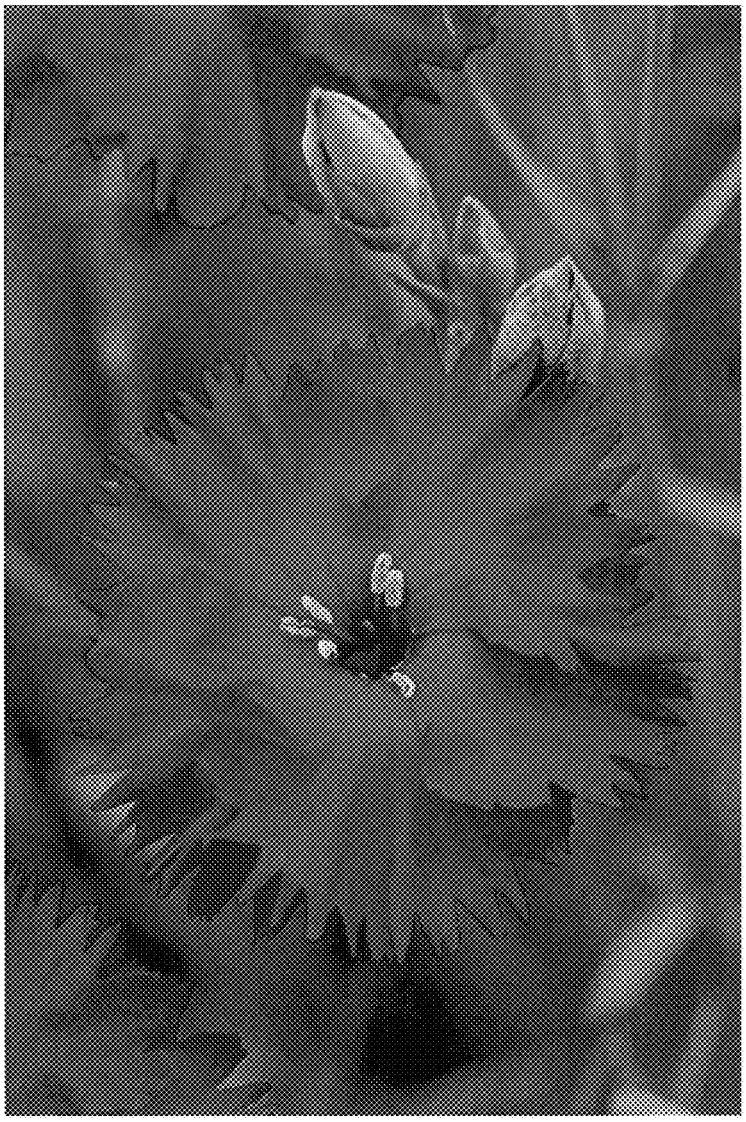
FIG. 2 depicts a close-up view of the flower of 'WP22 PIE68'.

Photographs were taken in May 2021 in Santa Barbara, Calif. of twelve-month old plants which have been grown outdoors in 2-gallon containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP22 PIE68'. Data was collected from plants grown in 3-liter containers under an unheated glasshouse in Ashcombe, Dawlish, United Kingdom. The color determinations are in accordance with the sixth edition (2015) of The Royal Horticultural Society Color Chart of The Royal Horticultural Society, London, England, except where general color terms of ordinary dictionary significance are used. No chemicals were used to treat the plants. Growing conditions are typical to other *Dianthus*.

Botanical classification: *Dianthus*.
- *Variety.*—'WP22 PIE68'.
- *Species.*—x *allwoodii*.
- *Common names.*—Hybrid *Dianthus*, Garden Pink.
- *Commercial classification.*—Hardy perennial.
- *Use.*—Ornamental plant for pots and containers.

Parentage: 'WP22 PIE68' is a hybrid plant that resulted from the controlled cross pollination between two *Dianthus* x *allwoodii* plants.
- *Female parent plant.*—'GI416' experimental *Dianthus* plant (unpatented).
- *Male parent plant.*—'GI539' experimental *Dianthus* plant (unpatented).

Plant description:
- *Bloom period.*—May to October.
- *Plant habit.*—Compact mounding habit.
- *Plant height.*—40 cm in overall height, including flower canopy.
- *Plant width.*—30 cm in width.
- *Plant hardiness.*—Hardy to minus 15° Centigrade.
- *Type.*—Perennial.
- *Root system.*—Fibrous.
- *Propagation.*—Propagation is accomplished using shoot cuttings.
- *Cultural requirements.*—Plant in full sun, well-drained and moderately fertile soil and keep well fertilized and watered.
- *Time required to produce a rooted cutting.*—5 weeks are needed to produce a rooted cutting.
- *Temperature recommended for cuttings to produce roots.*—The air temperature needed is a minimum of 15° Centigrade air temperature and base heat of 21° Centigrade.
- *Crop time.*—6 to 9 months is needed to produce a finished 3-litre container size from a well-rooted cutting.

Stem:
- *Shape.*—Cylindrical, solid.
- *Dimensions.*—12 cm in length, 4 mm diameter.
- *Surface.*—Glabrous and glaucous.
- *Color.*—145B, 145C and 145D (in the sheathing zone).
- *Branching.*—Numerous shoots from the axils of the lower leaves.
- *Internode length.*—3 mm to 5 mm between nodes (before extension of peduncle).
- *Node dimensions.*—4 mm in diameter and 4 mm in length.

Leaf:
- *Type.*—Evergreen.
- *Dimensions.*—11 cm in length, 3 mm in width.
- *Color adaxial surface.*—N189C.
- *Color abaxial surface.*—189A.
- *Shape.*—Linear.
- *Division.*—Simple.
- *Apex.*—Acute.
- *Base.*—Decurrent.
- *Venation.*—Absent on the adaxial surface and only one central vein visible on the abaxial surface.
- *Margins.*—Entire.
- *Attachment.*—Sheathing.
- *Arrangement.*—Opposite and spiraling up stem.
- *Surfaces* (*adaxial and abaxial*).—Glaucous.
- *Fragrance.*—Absent.

Flowers:
- *Inflorescence.*—Simple cyme.
- *Type.*—Single, polypetalous.
- *Number.*—6 to 7 per stem.
- *Dimensions* (*including calyx*).—38 mm in length and 48-55 mm in diameter.
- *Shape.*—Circular.
- *Lastingness.*—10 days at 20° Celsius on the plant; 8 to 10 days off the plant.
- *Fragrance.*—Medium, clove like.
- *Flowering period.*—May to October.

Peduncle:
- *Shape.*—Cylindrical, solid.
- *Dimensions.*—About 30 cm in length, 2 mm in diameter.
- *Surface.*—Glabrous, waxy.
- *Strength.*—Strong, rigid.
- *Color.*—122A.

Bud:
- *Shape.*—Oblong.
- *Color.*—N138C to N138D on apical half and 144C to 144D on basal half (below the bracts).
- *Anthocyanin.*—Sometimes present, as a very thin line along the edge of the lobes, 61A.
- *Dimensions.*—28 mm in length and 6 mm in width.

Petals:
- *Corolla.*—Upper part is flat and lower part of corolla is concave.
- *Petal arrangement.*—Persistent, apopetalous and overlapping.
- *Margin.*—Dentate.
- *Indentations.*—Irregular depth, up to 4 mm deep.
- *Texture.*—Soft.
- *Type.*—Single.
- *Number of petals.*—5.
- *Dimensions.*—53 mm in length, 33 mm in width.
- *Petal shape.*—Fan shape.
- *Petal surface* (*adaxial surface*).—Glabrous.
- *Petal surface* (*abaxial surface*).—Glabrous with sparse minute raised creases towards outermost petal margins.
- *Petal apex.*—Fan shaped, dentate.
- *Petal base.*—Strap shaped, tapering towards base.
- *Color pattern.*—Blade is vibrant magenta with iridescent overlapping central zone on young flowers only, color match not found, closest to 96D but lighter and hue like.
- *Petal color* (*adaxial surface*).—Ground color of blade: brighter and more iridescent than 71A. Color of middle of strap: 149D. Color of base of strap: 149D.

*Petal color* (*abaxial surface*).—Ground color of blade: 77B on the top section fading into 77C towards the strap. Color of middle of strap: 149D. Color of base of strap: 149D.

Calyx:

*Dimensions.*—28 mm in length and 8 mm in width.
*Shape.*—Cylindrical and straight.
*Sepals.*—5, fused up to 6 mm below the apex.
*Sepal dimensions.*—29 mm in length and 5 mm in width.
*Apex.*—Acute.
*Base.*—Truncate.
*Color of sepals, outer surface.*—N138C to N138D on apical half and 144C to 144D on basal half (below the bracts).
*Color of sepals, inner surface.*—139D.
*Anthocyanin.*—Sometimes present, as a very thin line along the apex, 61A.
*Splitting.*—Not observed.

Epicalyx:

*Number of Bracts.*—1 pair of 2.
*Bracts shape.*—Acute.
*Bracts dimensions.*—10 mm in length and 9 mm in width.
*Bracts color.*—122B, 122C and N138C are all present.
*Bracts anthocyanin.*—Absent.
*Number of bracteoles.*—1 pair of 2.
*Bracteoles shape.*—Acute.
*Bracteoles dimensions.*—10 mm in length and 11 mm in width.
*Bracteoles color.*—122B, 122C and N138C are all present.
*Bracteoles anthocyanin.*—Absent.

Reproductive organs:

*Stamen number.*—10.
*Stamen dimensions.*—33 mm length and 0.5 mm diameter.
*Color of filaments.*—Whiter than NN155A with a light purple section under the anthers, gradient from N75D to N75A (approximately 10 mm long under the anthers).
*Anther number.*—10.
*Anther dimensions.*—3 mm length and 1 mm in diameter.
*Color of anthers.*—77A to 77B (when fresh anthers).
*Anther attachment.*—Dorsifixed.
*Pollen.*—Present, nearest N82D.
*Style number.*—2.
*Style shoulder.*—Absent.
*Color of style.*—Whiter than NN155A.
*Style and Stigma dimensions.*—25 mm in length and 0.5 mm in width.
*Stigma number.*—One on each style.
*Stigma color.*—72B to 72C.
*Stigma dimensions.*—About 10 mm long along the top of the style, fimbriated zone.
*Ovary position.*—Superior.
*Ovary dimensions.*—9 mm in length and 5 mm in diameter.
*Ovary shape.*—Oblong.
*Ovary surface and texture.*—Smooth and slightly ribbed.
*Ovary color.*—NN144D at the uppermost surface and 145D at the lowest surface.

Seed:

*Color.*—202A.
*Length.*—4 mm.
*Diameter.*—3 mm.
*Shape.*—Oval and flattened.
*Surface.*—Crinkled.
*Number.*—Varies, up to 20 per pod.

Diseases and pests: Susceptible to known *Dianthus* pests and disease but no other susceptibilities to pests or disease are known.

COMPARISON WITH PARENTAL LINE AND KNOWN VARIETY

'WP22 PIE68' is distinguishable from the male parent as follows. The flower color of 'GI539' is self magenta light to medium and its vegetative part is slightly higher. The leaves of 'GI539' are also slightly broader than 'WP22 PIE68'.

'WP22 PIE68' is distinguishable from the female parent as follows. The female parent GI116 bears self dark pink flowers. Also, when grown outside, the overall flowering height of 'GI116' is higher than 'WP22 PIE68'.

The variety of *Dianthus* considered to most closely resemble 'WP22 PIE68' is *Dianthus* Plant Named 'WP19 PIE65' (U.S. Plant Pat. No. 32,445). In comparison with 'WP19 PIE65', 'WP22 PIE68' bears single vibrant magenta flowers with deep dentate petal edges. The leaves of 'WP22 PIE68' are also longer and thinner than 'WP19 PIE65'.

I claim:

1. A new and distinct cultivar of *Dianthus* plant named 'WP22 PIE68' as described and illustrated herein.

* * * * *